(12) United States Patent
Gross et al.

(10) Patent No.: US 9,642,860 B2
(45) Date of Patent: May 9, 2017

(54) COMBINATIONS OF CORROLES AND STATINS

(75) Inventors: Zeev Gross, Petach-Tikva (IL); Michael Aviram, Haifa (IL); Adi Haber, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 14/238,756

(22) PCT Filed: Aug. 14, 2012

(86) PCT No.: PCT/IB2012/054124
§ 371 (c)(1),
(2), (4) Date: Feb. 13, 2014

(87) PCT Pub. No.: WO2013/024425
PCT Pub. Date: Feb. 21, 2013

(65) Prior Publication Data
US 2014/0200204 A1 Jul. 17, 2014

Related U.S. Application Data (60) Provisional application No. 61/523,476, filed on Aug. 15, 2011.

(51) Int. Cl.
| | | |
|---|---|---|
| C07D 487/22 | (2006.01) |
| A61K 31/555 | (2006.01) |
| A61K 45/06 | (2006.01) |
| A61K 31/22 | (2006.01) |
| A61K 31/366 | (2006.01) |
| A61K 31/40 | (2006.01) |
| A61K 31/404 | (2006.01) |
| A61K 31/4418 | (2006.01) |
| A61K 31/47 | (2006.01) |
| A61K 31/505 | (2006.01) |
| A61K 31/405 | (2006.01) |

(52) U.S. Cl.
CPC ........... *A61K 31/555* (2013.01); *A61K 31/22* (2013.01); *A61K 31/366* (2013.01); *A61K 31/40* (2013.01); *A61K 31/404* (2013.01); *A61K 31/405* (2013.01); *A61K 31/4418* (2013.01); *A61K 31/47* (2013.01); *A61K 31/505* (2013.01); *A61K 45/06* (2013.01)

(58) Field of Classification Search
CPC .................................................. C07D 487/22
See application file for complete search history.

(56) References Cited

U.S. PATENT DOCUMENTS

| | | |
|---|---|---|
| 6,541,628 B1 | 4/2003 | Gross et al. |
| 6,730,666 B1 | 5/2004 | Yayon et al. |
| 2004/0180872 A1 | 9/2004 | Gross et al. |
| 2009/0005425 A1 | 1/2009 | Woo et al. |
| 2010/0305335 A1 | 12/2010 | Palmer et al. |
| 2010/0323981 A1 | 12/2010 | Linnane |

(Continued)

FOREIGN PATENT DOCUMENTS

| | | |
|---|---|---|
| JP | 2004531468 | 10/2004 |
| JP | 2009521526 | 6/2009 |
| KR | 20080107129 | 12/2008 |

(Continued)

OTHER PUBLICATIONS

Blum et al. Dual Therapy With Statins and Antioxidants Is Superior to Statins Alone in Decreasing the Risk of Cardiovascular Disease in a Subgroup of Middle-Aged Individuals With Both Diabetes Mellitus and the Haptoglobin 2-2 Genotype Arteriosclerosis, Thrombosis, and Vascular Biology, 2008, 28: e18-20.*
Wali et al. (Lipids, 2007, 42, 1113). Synergistic Antiproliferative Effects of c-Tocotrienol and Statin Treatment on Mammary Tumor Cells.*
Okello et al. (Medical Hypotheses, 2009, 73, 306). Combined statin/coenzyme Q10 as adjunctive treatment of chronic heart failure.*
Qureshi et al., Synergistic effect of tocotrienol-rich fraction (TRF25) of rice bran and lovastatin on lipid parameters in hypercholesterolemic humans ,Journal of Nutritional Biochemistry 12, 2001, 318-329.*

(Continued)

*Primary Examiner* — Brian McDowell
(74) *Attorney, Agent, or Firm* — A.C.Entis-IP Ltd.

(57) ABSTRACT

Embodiments of the invention relate to methods of treatment a cardiovascular disease in a patient comprising administering an effective amount of a statin or a pharmaceutically acceptable salt thereof in combination with an effective amount of a transition metal complex of a corrole, an optically active isomer thereof or a pharmaceutically acceptable salt thereof. Further embodiments refer to pharmaceutical compositions comprising a statin and a corrole. Optionally, the corrole has a structure:

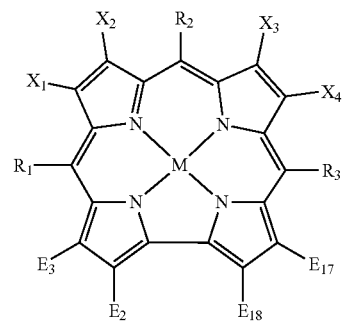

wherein;
M is a transition metal selected from the group consisting of Mn, Fe, Ru, Co, V, Cr, and Cu and $R_1$, $R_2$, $R_3$, $X_1$, $X_2$, $X_3X_4$; $E_2$, $E_3$, $E_{17}$ and $E_{18}$ are each defined as in the specification.

13 Claims, 3 Drawing Sheets

(56) References Cited

U.S. PATENT DOCUMENTS

2012/0269890 A1    10/2012    Maya Ayala et al.

FOREIGN PATENT DOCUMENTS

| WO | 0243721 | | 6/2002 |
| --- | --- | --- | --- |
| WO | 2009027965 | | 3/2009 |
| WO | WO2009/027965 | * | 3/2009 |
| WO | 2009095923 | | 8/2009 |

OTHER PUBLICATIONS

Haber, A. et. al., "Amphiphilic/Bipolar Metallocorroles That Catalyze the Decomposition of Reactive Oxygen and Nitrogen Species, Rescue Lipoproteins from Oxidative Damage,and Attenuate Atherosclerosis in Mice", Agnew. Chem. Int. Ed. 47 (2008); pp. 7896-7900.

Haber, A. et. al., "Protecting the beneficial functionality of lipoproteins by 1-Fe, a corrole-based catalytic antioxidant", Chem. Sci. 2 (2011): (2), pp. 295-302.

Mahammed, A. et. al., "Albumin-conjugated Corrole metal complexes: extremely simple yet very efficient biomimetic oxidation systems". J. Am. Chem. Soc. vol. 127, No. 9, (2005), pp. 2883-2887.

Rosanoff, A. et. al., "Comparison of Mechanism and Functional Effects of Magnesium and Statin Pharmaceuticals", J Am. Coll. Nutr. 23 No. 5 (2004); pp. 501S-505S Fuhrman, B. et. al., "Oxidative stress increases the expression of the CD36 scavenger receptor and the cellular uptake of oxidized low-density lipoprotein in macrophages from atherosclerotic mice: protective role of antioxidants and of paraoxonase", Atherosclerosis 161 (2002); pp. 307-316.

Chandra, B. et. al., "Inhibitory effect of metalloporphyrins in conjuction with cholesterol on hepatic phospholipase A2 activity in-vivo in rats", A. Indian J. Clin. Biochem. 15 No. 2 (2000); pp. 148-154.

Preiss, D. et. al., "Risk of Incident Diabetes With Intensive-Dose Compared With Moderate-Dose Statin Therapy", JAMA vol. 305, No. 24 (2011); pp. 2556-2564.

Tousoulis,D. et. al., "Effects of combined administration of low dose atorvastatin and vitamin E on inflammatory markers and endothelial function in patients with heart failure", The European Journal of Heart Faliure 7 (2005); pp. 1126-1132.

Waters, D.D. et. al., "Predictors of new-onset diabetes in patients treated with atorvastatin: results from 3 large randomized clinical trials.", J Am Coll Cardiol 57 (2011); pp. 1535-1545.

Aviv-Harel, I. et al. "Aura of Corroles". Chem. Eur. J. (15), 2009; pp. 8382-8394.

Saltsman, I. et. al., "Selective Substitution of Corroles: Nitration, Hydroformylation, and Chlorosulfonation", J. Am. Chem. Soc. 124 No. 25 (2002); pp. 7411-7420.

Verschuren, L. et. al., "A Dietary Mixture Containing Fish Oil, Resveratrol, Lycopene, Catechins, and Vitamins E and C Reduce Atherosclerosis in Transgenic Mice.", The Journal of Nutrition: Nutrition and Disease, 141 No. 5 (2011); pp. 863-869.

Aviram, M. et. al., "Oxidative stress and macrophage foam cell formation during atherosclerosis development", Free Radical Biol. Med. 37 (2004); pp. 1304-1316.

Cheung, M.C. et. al. ,"Antioxidant Supplements Block the Response of HDL to Simvastatin-Niacin Therapy in Patients With Coronary Artery Disease and Low HDL" Arterioscler. Thromb. Vasc. Biol. 21 (2001); pp. 1320-1326.

Kleemann, R. et. al. "HMG-CoA Reductase Inhibitors: Effects on Chronic Subacute Inflammation and Onset of Atherosclerosis Induced by Dietary Cholesterol" Current Drug Targets—Cadiovas. & Hemat. Dis. 5 (2005); pp. 441-453.

Smith, J.D. "Dysfunctional HDL as a Diagnostic and Therapeutic Target" Arterioscler. Throm. Vasc. Biol., No. 30 (2010); pp. 151-155.

International search report for PCT/IB2012/054124 mailing date Dec. 12, 2012.

J. Newton, "Iron Complex Could Prevent Cardiovascular disease", Chem. Sci. 12 (2010), retrieved from the internet: http://www.rsc.org/Publishing/ChemScience/Volume/2010/12/iron_complex_asp (retrieved on Nov. 23, 2012).

Kloosterman, K.; "Israel-US Team Kills Breast Cancer in the Dark", Arutz Sheva News, Jun. 12, 2009, retrieved from the internet: URL: http://www.israelnationalnews.com/Controls/SendFreind.ashx?print=1&type=0&item=131839 (retrieved on Nov. 23, 2012).

EP Office Action dated Jan. 12, 2016 for Application No. 12769733.2, filed Mar. 14, 2014.

2nd Chinese Office Action dated Dec. 8, 2015 for Application No. 201280050749.6, filed Apr. 15, 2014.

Milman, Uzi et al.; Vitamin E Supplementation Reduces Cardiovascular Events in a Subgroup of Middle-Aged Individuals with Both Type 2 Diabetes Mellitus and the Haptoglobin 2-2 Genotype, A Prospective Double-Blinded Clinical Trial; Arterioscler Thromb Vasc. Biol.; American Hear Association, Inc. 2008 (downloaded on Feb. 24, 2016 from http://atvb.ahajournals.org/) ; pp. 341-347 and online data supplement.

Blum Shany et al, Dual Therapy With Statins and Antioxidant Is Superior to Statins Alone in Decreasing the Risk of Cardiovascular Disease in a Subgroup of Middle-Aged Individuals With Both Diabetes Mellitus and Haptoglobin 2-2 Genotype, (2008) Arterioscler. Thromb. & Vasc. Biol. vol. 28 pp. 18-20.

Foster T. et al, Atrovastatin and Antioxidants for the Treatment of Nonalcoholic Fatty Liver Disease: The St Frances Heart Study Randomized Clinical Trial, Am J Gastroenerol (2011) vol. 106 pp. 71-77.

Dobiasova M. et al., Cholesterol esterification and atherogenic index of plasma correlate with lipoprotein size and findings on coronary angiography, J Lipid Res (2011) vol. 52, pp. 566-571.

Zadelaar, S., et. al. "Mouse Models for Atherosclerosis and Pharmaceutical Modifiers" (2007) Arterioscler Thromb Vasc Biol., 2007, vol. 27, pp. 1706-1721.

Japanese Office Action dated Jun. 23, 2016 for Application No. 2014-525542, filed Feb. 13, 2014.

Israel Office Action dated Sep. 6, 2016 for Application No. 230988, filed Feb. 13, 2014.

Peter H. Stone et al., Effect of Intensive Lipid Lowering, With or Without Antioxidant Vitamins, Compared With Moderate Lipid Lowering on Myocardial Ischemia in Patients With Stable Coronary Artery Disease the Vascular Basis for the Treatment of Myocardial Ischemia Study, Coronary Heart Disease, Apr. 4, 2005, pp. 1748-1755.

B. Greg Brown et al., Simvastatin and Niacin, Antioxidant Vitamins, or the Combination for the Prevention of Coronary Disease, The New England Journal of Medicine, vol. 345, Nov. 29, 2001 No. 22, pp. 1583-1592.

Jian-Ming Lo et al., Chemical and molecular mechanisms of antioxidants: experimental approaches and model systems, Molecular Medicine, vol. 14, No. 4, 2010, pp. 840-860.

Maret G. Traber et al., Vitamin E, Antioxidant and Nothing More, Free Radic Biol Med. Jul. 1, 2007; 43(1): 4-15, pp. 1-19.

William R. Greco et al., The Search for Cytotoxic Synergy Between Anticancer Agents: a Case of Dorothy and the Ruby Slippers, Editorials, Journal of the National Cancer Institute, vol. 88, No. 11, Jun. 5, 1996, pp. 699-700.

Richard Deichmann et al., Coenzyme Q10 and Statin-Induced Mitochondrial Dysfunction, Academic Division of Ochsner Clinic Foundation, The Ochsner Journal 10: 2010, pp. 16-21.

Liu, Xuehui, Contemporary Medicine, vol. 16, No. 14, pp. 37-39; published on May 31, 2010.

First Office Action dated Apr. 3, 2015 for corresponding Chinese application; Serial No. 2012800507496 filed Aug. 15, 2012.

Mexican Office Action dated Dec. 7, 2016 for Application No. MX/a/2014/001823, Filed Feb. 14, 2014.

Japanese Office Action dated Dec. 16, 2016 for Application No. 2014-525542, filed Feb. 13, 2014.

* cited by examiner

COMBINATIONS OF CORROLES AND STATINS

RELATED APPLICATIONS

This application is a National Phase of PCT Patent Application No. PCT/IB2012/054124 having International filing date of Aug. 14, 2012, which claims the benefit of priority under 35 USC §119(e) of U.S. Provisional Patent Application No. 61/523,476 filed on Aug. 15, 2011. The contents of the above applications are all incorporated by reference as if fully set forth herein in their entirety.

TECHNICAL FIELD

Embodiments of the invention relate to a drug combination comprising a corrole and a statin.

BACKGROUND

Cardiovascular disease (CVD) is a class of diseases that involves the heart and/or blood vessels. This class of diseases is a leading cause of morbidity and mortality worldwide. The most prominent CVD is atherosclerosis, a condition in which an artery wall thickens as a result of accumulation of fatty materials therein. As atherosclerotic plaques develop they may cause complete closure of the artery lumen, resulting in insufficient blood supply to downstream tissues. Such blockage commonly occurs in coronary arteries or in the arteries of the brain, resulting in myocardial infarction or stroke, respectively.

Lipidic materials, including cholesterol, are transported in the circulatory system by lipoproteins, of which two major classes are high density lipoproteins (HDL) and low density lipoproteins (LDL). HDL is commonly referred to as "good cholesterol" as it operates to remove excess cholesterol from the arteries and transport it to the liver. LDL is commonly referred to as "bad cholesterol", as it delivers cholesterol to the tissues, thus contributing to cholesterol accumulation in arterial macrophages, a first step in the development of atherosclerotic plaques. Patients with cholesterol levels higher than normal, in particular LDL cholesterol, a condition commonly referred to as hypercholesterolemia, are at high risk of developing atherosclerosis. One of the ways to control hypercholesterolemia is to limit dietary cholesterol intake. However, in many patients, controlling dietary cholesterol intake is not sufficient in reducing cholesterol levels. Medications such as statins are commonly administered to patients with hypercholesterolemia in order to lower the risk of CVD.

Statins are compounds which inhibit the enzyme HMG-CoA reductase, a key enzyme in the de novo synthesis of cholesterol, thereby lowering the production of cholesterol within the cells (A. Rosanoff 2004). This causes increased cholesterol uptake from the bloodstream to the cells, thus lowering serum cholesterol and the risk of CVD. The first statin marketed was lovastatin, which was isolated from the fungus *Aspergillus terreus* and marketed by Merck & Co. Other statins were identified in naturally occurring fungi such as oyster mushrooms and red yeast rice. After lovastatin, other statins were developed and their use became common among hypercholesterolemia patients and patients at high risk of CVD. Additional statins include atorvastatin, cerivastatin, fluvastatin, mevastatin, pitavastatin, pravastatin, rosuvastatin and simvastatin. Statins are now the most prescribed drugs worldwide.

In addition to lipoprotein concentration in the blood, lipoprotein oxidation also plays a major role in the development of atherosclerosis. Oxidized LDL (oxLDL) is taken up by arterial macrophages in a non-controlled fashion, thus leading to accumulation of cholesterol in the arteries (B. Fuhrman 2002). In addition, beneficial anti-atherogenic effects of HDL are impaired upon its oxidation (Smith 2010). Antioxidants that reduce oxidation of LDL and HDL were found to have an in vivo effect in reducing atherosclerosis. For example, a mixture of antioxidants lycopene, resveratrol, catechin and vitamins E and C reduced atherosclerosis in transgenic mice (L. Verschuren 2011).

Although statins and antioxidants were shown to have a beneficial effect on atherosclerosis and on coronary heart disease, when statins were administered in combination with some antioxidants, not only did there appear to be an absence of benefit from the combinations relative to the use of each component alone, but the components of the combinations appeared to interfere with each other. The combinations appeared less effective as anti-atherosclerotic agents than the statins and the antioxidants when not administered in combination. For example, in patients with low HDL, beneficial effects of simvastatin and niacin were blunted when compared to a group of patients receiving simvastatin/niacin in combination with the antioxidants beta-carotene, vitamin C, vitamin E, and selenium (M. C. Cheung 2001). Another study showed that patients receiving atorvastatin in combination with the antioxidant vitamin E experienced less of a reduction in the expression of pro-inflammatory cytokines than patients receiving atorvastatin alone (D. Tousoulis 2005).

SUMMARY

An embodiment of the invention provides a method for treating a CVD in a subject comprising administering an effective amount of a statin or a pharmaceutically acceptable salt thereof in combination with an effective amount of a transition metal complex of a corrole, an optically active isomer thereof, or a pharmaceutically acceptable salt thereof.

Corroles are organic molecules having a contracted porphyrin ring comprising nineteen carbon atoms and 4 nitrogen atoms, and are capable of binding transition metals. Transition metal complexes of corroles were found to have an antioxidant effect. The iron(III) complex of a corrole whose structural formula is depicted below, also known as 1-Fe, is a potent catalytic antioxidant (I. Aviv-Harel 2009).

It has been shown that 1-Fe spontaneously conjugates to HDL and LDL to protect them against oxidation and nitration (A. Haber 2008)(A. Haber 2011). Unlike other antioxidants which seem to interfere with the action of statins, corroles have been shown by the inventors to synergistically lower cholesterol levels when used in combination with statins.

"In combination" refers to both drugs being substantially effective in the body at a same time. Both drugs can be administered substantially at the same time, or both drugs can be administered at different times but have effect on the body at the same time. For example, "in combination" includes administering a corrole before the administration of the statin, and subsequently administering the statin while functioning of the corrole in the body is substantially extant.

An embodiment of the invention provides a pharmaceutical composition for delivering a statin and a corrole in combination. The composition optionally comprises: a transition metal complex of a corrole, an optically active isomer thereof, or a pharmaceutically acceptable salt thereof; a statin or a pharmaceutically acceptable salt thereof; and at least one pharmaceutically acceptable carrier.

A method for treating CVD using a combination of a statin and a corrole in accordance with an embodiment of the invention appears more effective than treatment of CVD with either a statin without a corrole or with a corrole without a statin. It appears that methods in accordance with an embodiment of the invention can provide beneficial therapeutic effects in treating CVD using relatively reduced dosages of statins, potentially ameliorating side effects associated with statins.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

This summary is provided to introduce a selection of concepts in a simplified form that are further described below in the detailed description. This summary is not intended to identify key features or essential features of the claimed subject matter, nor is it intended to be used to limit the scope of the claimed subject matter.

DETAILED DESCRIPTION

The administration of two drugs to treat a given condition raises a number of potential problems. When two drugs are introduced into the body, each drug can affect the absorption, distribution, and elimination of the other and hence, alter the effects of the other. Thus, when two drugs are administered to treat the same condition, it may be unpredictable whether each will complement, have no effect on, or interfere with, the therapeutic activity of the other in a human subject. For example, as noted above, even though both statins and antioxidants when administered independently of each other appeared beneficial in combating atherosclerosis, when administered in combination they reduced each other's beneficial effects.

Statins are currently approved for use in many dosages. It is recommended for patients to start statin therapy at lower dosages, for example, 10-20 milligrams (mg) daily of simvastatin, and increase dosage if the lower dosages are ineffective after being administered for a time. Certain patients having a high risk of CVD are recommended to start therapy at a moderate dose, for example, 40 mg of simvastatin daily. Statins as monotherapy, although approved for treatment of CVDs, are associated with health risks and potential side effects. The US Food and Drug Administration recently issued a safety announcement warning the public about an increased risk of muscle injury in patients taking the highest approved dose (80 mg) of simvastatin (FDA n.d.). In addition, taking high doses of 80 mg of simvastatin or atorvastatin increases the chance of developing Type 2 diabetes by 12 percent over five years compared to taking moderate dose statins (D.D. Waters 2011) (D. Preiss 2011).

When treating CVD with a combination of a statin or a pharmaceutically acceptable salt thereof in combination with an effective amount of a transition metal complex of a corrole, an optically active isomer thereof or a pharmaceutically acceptable salt thereof according to an embodiment of the invention, a smaller dosage of the statin may be needed to obtain a same therapeutic effect than when the statin is administered without the corrole. Therefore, the side effects associated with statin treatment when treating according to an embodiment of the invention may be reduced. For example, the beneficial effects of high dosage statin therapy may be obtained without the associated side effects by administering a moderate or low dose of a statin in combination with a transition metal complex of a corrole. In an embodiment of the invention the statin is selected from the group consisting of: atorvastatin, cerivastatin, fluvastatin, lovastatin, mevastatin, pitavastatin, pravastatin, rosuvastatin and simvastatin.

Pharmaceutical compositions comprising corroles have been disclosed in U.S. Pat. No. 6,730,666, incorporated herein by reference. Methods of manufacture of corroles are described in U.S. Pat. No. 6,541,628, incorporated herein by reference.

In an embodiment of the invention the transition metal complex of a corrole has the formula:

wherein $R_1$, $R_2$ and $R_3$ are each independently a carbocyclic aryl ring or a heterocyclic aryl ring, each ring comprising 5 or 6 atoms;

M is a transition metal selected from the group consisting of Mn, Fe, Ru, Co, V, Cr, and Cu;

$X_1$, $X_2$, $X_3$ and $X_4$ are each independently H or a halogen;

$E_2$, $E_3$, $E_{17}$ and $E_{18}$ are each independently H, halogen, $SO_2Cl$, $SO_3H$, $SO_2NR_4R_5$, $CO_2H$, $CO_2R$, $COCl$, $CONR_4R_5$, CHO, $CH=C(CO_2H)_2$, $CH=C(CN)CO_2H)$, or $NO_2$, R is alkyl or aryl and $R_4$ and $R_5$ are each independently H, alkyl, aryl or together with the N atom to which they are attached form a saturated 5-6 membered ring optionally containing an additional heteroatom selected from the group consisting of O, S and N.

In an embodiment of the invention, the transition metal is Fe; $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H.

In an embodiment of the invention, the transition metal is Fe; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H.

In an embodiment of the invention, the transition metal is Mn; $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H.

In an embodiment of the invention, the transition metal is Mn; $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H.

In an embodiment of the invention a transition metal complex of a corrole, an optically active isomer thereof or a pharmaceutically acceptable salt thereof is administered in the same dosage form as a statin or a pharmaceutically acceptable salt thereof.

In an embodiment of the invention a transition metal complex of a corrole, an optically active isomer thereof or a pharmaceutically acceptable salt thereof is administered in a different dosage form than a statin or a pharmaceutically acceptable salt thereof. In an embodiment of the invention, the statin or pharmaceutically acceptable salt thereof is administered at the same time as the transition metal complex of a corrole, an optically active isomer thereof or a pharmaceutically acceptable salt thereof. In an embodiment of the invention, the statin or pharmaceutically acceptable salt thereof is administered before the transition metal complex of a corrole, an optically active isomer thereof or a pharmaceutically acceptable salt thereof. In an embodiment of the invention, the statin or pharmaceutically acceptable salt thereof is administered after the transition metal complex of a corrole, an optically active isomer thereof or a pharmaceutically acceptable salt thereof.

In an embodiment of the invention, the transition metal complex of a corrole, an optically active isomer thereof or a pharmaceutically acceptable salt thereof and a statin or a pharmaceutically acceptable salt thereof are each administered via oral, rectal, vaginal, topical, nasal, ophthalmic, transdermal, subcutaneous, intramuscular, intraperitoneal or intravenous routes of administration.

The pharmaceutical compositions according to an embodiment of the invention are conveniently presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe.

The compositions of the present invention are generally administered in the form of a pharmaceutical composition comprising at least one of the active components (corrole or statin) of this invention together with a pharmaceutically acceptable carrier or diluent. Thus, the compositions of this invention can be administered either individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the components of this invention can be combined with various sweetening agents, flavoring agents, coloring agents, emulsifying agents and/or suspending agents, as well as such diluents as water, ethanol, propylene glycol, glycerin and various like combinations thereof.

The combinations according to embodiments of this invention may also be administered in a controlled release formulation such as a slow release or a fast release formulation. Such controlled release dosage formulations of the combinations of this invention may be prepared using methods well known to those skilled in the art.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

Pharmaceutical compositions according to embodiments of the invention may contain 0.1%-95% of the active components(s) of this invention, preferably 1%-70%. In any event, the composition or formulation to be administered may contain a quantity of active components according to embodiments of the invention in an amount effective to treat the condition or disease of the subject being treated.

Since embodiments of the present invention relate to the treatment of diseases and conditions with a combination of active ingredients which may be administered separately, separate pharmaceutical compositions may be packaged in kit form. The kit may comprise two separate pharmaceutical compositions, a corrole and a statin. The kit form is particularly advantageous when the separate components are preferably administered in different dosage forms (e.g., oral and parenteral), are administered at different dosage intervals, or when titration of the individual components of the combination is desired by the prescribing physician.

In an embodiment of the invention, the daily dosage of the transition metal complex of a corrole, an optically active isomer thereof or a pharmaceutically acceptable salt thereof is between 0.1 mg and 1500 mg (expressed in terms of active corrole equivalent in the case of a salt). In embodiments of the invention, the daily dosage of the statin is administered in accordance with table 1 below:

TABLE 1

| Statin | Salt | Daily dosage (in mg statin or statin equivalent in the case of a salt) |
|---|---|---|
| Atorvastatin | Calcium | 10, 20, 40 or 80 |
| Cerivastatin | Sodium | 0.05, 0.1, 0.2, 0.3, 0.4 or 0.8 |
| Fluvastatin | Sodium | 20, 40 or 80 |
| Lovastatin | (none) | 10, 20, 40, 60 |
| Mevastatin | (none) | 10-50 |
| Pitavastatin | Calcium | 1, 2 or 4 |
| Pravastatin | Sodium | 10, 20, 30, 40 or 80 |
| Rosuvastatin | Calcium | 5, 10, 20 or 40 |
| Simvastatin | (none) | 10, 20, 40 or 80 |

In embodiments of the invention, the daily dosage of the statin is administered in dosages lower than the dosages listed in Table 1.

In an embodiment of the invention, the statin is administered before bedtime.

An embodiment of the invention provides a method for treating a CVD in a patient comprising administering an effective amount of a statin or a pharmaceutically acceptable salt thereof in combination with an effective amount of an anti-oxidant that is a transition metal complex of a corrole, an optically active isomer thereof or a pharmaceutically acceptable salt thereof, in combination with niacin.

An embodiment of the invention provides a method for treatment of a CVD in a subject comprising administering an effective amount of a transition metal complex of a corrole, an optically active isomer thereof or a pharmaceutically acceptable salt thereof in combination with a statin or a pharmaceutically acceptable salt thereof, wherein the CVD is selected from the group consisting of: coronary heart disease, primary hyperlipidemia, mixed dyslipidemia, hypertriglyceridemia, dysbetalipoproteinemia, homozygous familial hypercholesterolemia, heterozygous familial hypercholesterolemia, atherosclerosis, congestive heart failure, myocardial infarction, myocardial ischemia and reperfusion.

An embodiment of the invention provides a method for treatment of a CVD in a subject having a risk factor associated with CVD comprising administering an effective amount of a transition metal complex of a corrole, an optically active isomer thereof or a pharmaceutically acceptable salt thereof in combination with a statin or a pharmaceutically acceptable salt thereof, wherein the risk factor associated with CVD is selected from the group consisting of: elevated total cholesterol, elevated LDL cholesterol, elevated VLDL cholesterol, elevated apolipoprotein B, elevated triglycerides, decreased HDL cholesterol, elevated oxidized HDL, elevated oxidized LDL, obesity, smoking, type 2 diabetes, type 1 diabetes, history of myocardial infarction, history of revascularization procedures, history of stroke and history of angina.

EXAMPLE 1

Cholesterol Biosynthesis Model

Accumulation of cholesterol within arterial macrophages is a step in the development of atherosclerosis (M. Aviram 2004). Statins can lower the levels of cholesterol biosynthesis in arterial macrophages. The cholesterol biosynthesis model which was employed determined the effect of various agents (pravastatin alone, fluvastatin alone, 1-Fe alone in various concentrations, 1-Fe in combination with pravastatin and 1-Fe in combination with fluvastatin) on reduction of cholesterol biosynthesis in macrophages.

Murine J774.A1 macrophages were cultured in DMEM (Dulbecco's Modified Eagle Medium) containing 5% FCS (fetal calf serum) in a humidified incubator. 1-Fe was prepared in accordance with known procedures (A. Mahammed 2005) (I. Saltsman 2002). The effect of different concentrations of 1-Fe on cholesterol biosynthesis from acetate and on 1-Fe cellular uptake were determined by incubating J774.A1 macrophages for 24 h (hours) with 0, 5, 20 or 50 µM (micromolar) of 1-Fe. Intracellular corrole concentrations were then determined by a chemiluminescent method, and cholesterol biosynthesis was assayed by measuring acetate incorporation into cholesterol. The chemiluminescent method involved rupturing cells and checking emission at 430 nm (nanometers) after the addition of 1 mM (millimolar) luminol and 10 mM $H_2O_2$ (pH=13) to the ruptured cells. Acetate incorporation into cholesterol was performed by incubating cells overnight with DMEM containing 2% BSA (bovine serum albumin), followed by incubation with isotopically labeled [$^3$H]acetate (1 millicurie/milliliter) (Amersham International, Bucks, UK) in DMEM containing 2% BSA for 3 h at 37° C. (degrees Celsius). Cellular lipids were then extracted in hexane:isopropanol (3:2, volume ratio), and the upper phase separated by thin layer chromatography (TLC) on silica gel plates with hexane:ether:acetic acid (80:20:1.5, volume ratio). Unesterified cholesterol spots were visualized by iodine vapor (using appropriate standard), scraped into scintillation vials and counted in a β-counter. 0.1 M (molar) NaOH (sodium hydroxide) was added to the remains of the cells, and cellular proteins were measured the following day by the Lowry method.

Figure 1A:
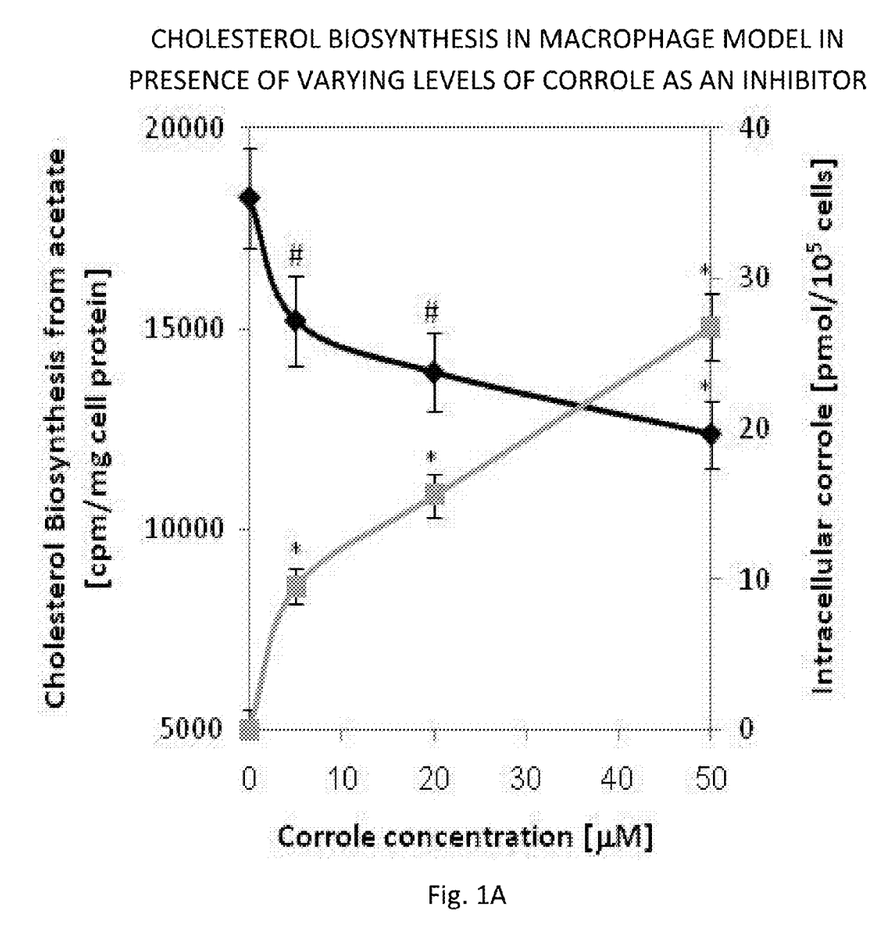
FIG. 1A shows a graph depicting cholesterol biosynthesis relative to corrole dosage and corrole intracellular concentration in J774.A1 macrophages.

As seen in the solid line in FIG. 1A, the amounts of cholesterol synthesized from acetate by the macrophages (expressed in counts per minute/mg of cell protein) decreased as the dosage of 1-Fe increased, in parallel with the increase in 1-Fe cellular uptake (indicated by broken line, measured in terms of picomoles of 1-Fe per $10^5$ cells) indicating a dose dependent effect of 1-Fe on inhibition of cholesterol biosynthesis. This is in sharp contrast with studies of metalloporphyrins, the most closely related class of compounds (in terms of structure and activity), which actually increase hepatic cholesterol levels in treated rats (Chandra 2000).

In order to determine the combined effects of statins and 1-Fe on cholesterol biosynthesis, J774.A1 macrophages ($2\times10^6$ cells/well) were incubated for 24 h in the absence of a corrole and a statin (control) or with the following agents: 20 µM 1-Fe alone, 200 µM pravastatin (PS), 20 µM 1-Fe with 200 µM PS, 20 µM fluvastatin (FS), or 20 µM 1-Fe with 20 µM FS. After removal of the non-internalized fraction of the test compounds, cholesterol biosynthesis from acetate was determined as described above.

Figure 1B:
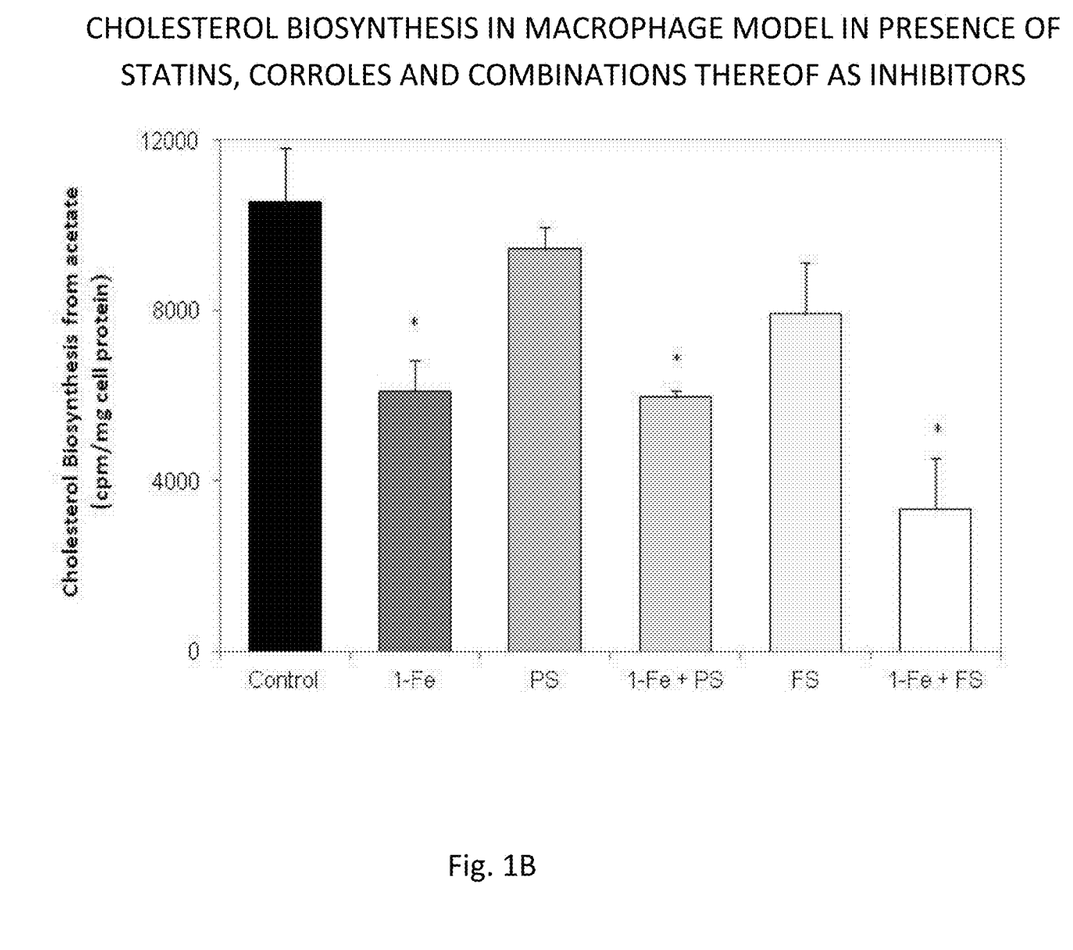
FIG. 1B shows a histogram depicting cholesterol biosynthesis in J774.A1 macrophages in absence of a pharmaceutical agent and in the presence of a corrole (1-Fe), a statin (fluvastatin [FS] or pravastatin [PS]) and combinations of a corrole and a statin (FS or PS)

The reduction of macrophage biosynthesis of cholesterol was determined to be 35% for 1-Fe alone, 10% for PS alone, 45% for 1-Fe and PS, 25% for FS alone and 70% for 1-Fe and FS. The results are depicted in FIG. 1B. The results show the combined positive effect of 1-Fe with either one of the statins, and suggest that as opposed to other antioxidants that hinder the activity of statins, the combination of corroles and statins may reduce cholesterol biosynthesis much beyond the level feasible by statins alone.

As corrole treatment addresses the problem of oxidation of cholesterol, its administration may improve not only cholesterol quantities, but also may improve the quality of lipoproteins by reducing the amount of oxLDL and oxHDL due to the pronounced catalytic antioxidant activity of the corrole.

EXAMPLE 2

Corrole-Statin Synergism

Mevalonic acid serves as one of the precursors to cholesterol biosynthesis in humans. Mevalonic acid is synthesized from 3-hydroxy-3methylglutaryl-CoA (HMG-CoA) and nicotineamide adenine dinucleotide phosphate (NADPH) in a reaction catalyzed by the enzyme HMG-CoA reductase (HMGCR). It is suggested by the inventors that both statins and corroles have an inhibitory effect on the reaction catalyzed by the enzyme HMGCR, thereby reducing mevalonic acid synthesis which in turn reduces cholesterol biosynthesis.

The effects of 1-Fe and statins fluvastatin and pravastatin alone and in combination on mevalonic acid production were tested using the following in vitro method.

Figure 2A:
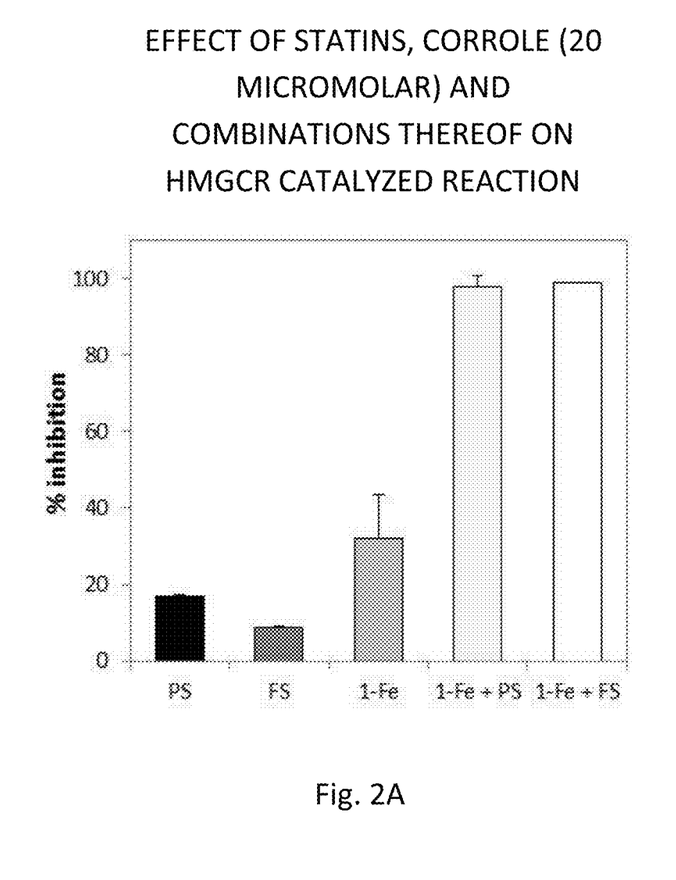
FIGS. 2A and 2B show histograms depicting effect of 20 micromolar 1-Fe (2A), 15 micromolar 1-Fe (2B), FS, PS and combinations of 1-Fe and FS or PS on inhibition of an HMG-CoA reductase-catalyzed reaction, an enzyme induced biochemical reaction through which a precursor to cholesterol is formed in humans.
Figure 2B:
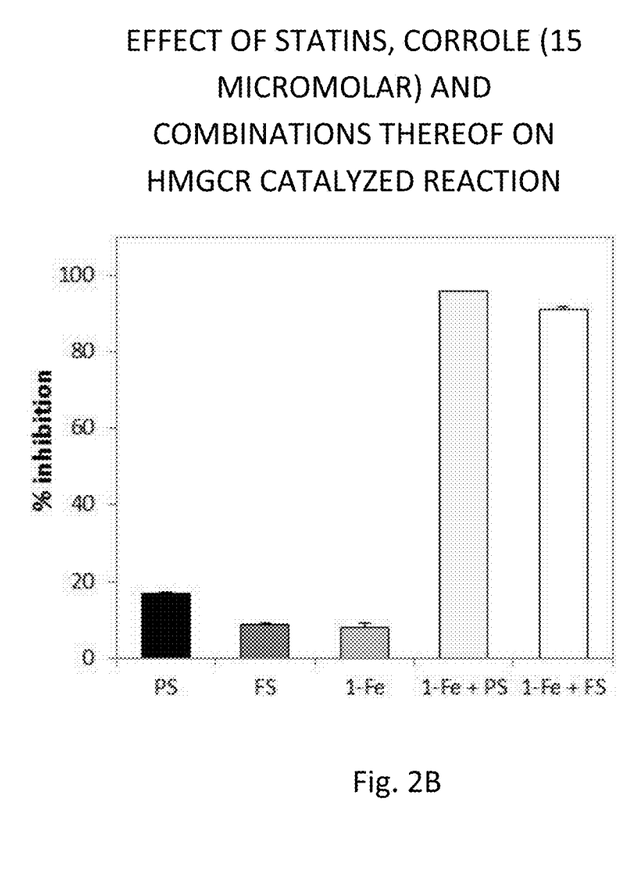

Substrates of the HMGCR catalyzed reaction, NADPH (400 μM] and HMGCR (200 μM) were mixed in activity buffer comprising 100 mM sodium phosphate buffer, 1 mM ethylenediaminetetraacetic acid (EDTA), 10 mM dithiothreitol, 2% dimethyl sulfoxide, and 1 mM magnesium sulphate, the mixture having a pH of 6.8. 1-Fe, PS, or FS (alone or as a corrole statin combination) were added to the substrate mixture at various concentrations, followed by addition of HMGCR (0.48 μM). Reactions were then incubated at 37° C. for 15 minutes, followed by injection of 80 μl (microliter) to a reverse phase GraceSmart RP18 high performance liquid chromatography column (HPLC). The column was eluted with 10 mM ammonium acetate buffer with a pH of 5.8-6 containing 10 mM tetrabutyl ammonium acetate and acetonitrile in varying concentrations. As mevalonate concentration is difficult to identify in reaction mixture because it has no absorbance in the UV range, the yield of each reaction was calculated from the amount of CoA byproduct formed in the reaction after subtracting the baseline amount of CoA present as an impurity in the commercial HMG-CoA determined by injecting the substrate mixture alone. The inhibition percentage was calculated from the yield of each reaction relative to the yield of the enzymatic reaction without the addition of inhibitor. Table 2 lists average inhibition percentages for each inhibitor in two separate tests that were each performed in triplicate. The results are also shown in FIGS. 2A and 2B.

TABLE 2

| Inhibitor concentrations in micromolar | | | |
|---|---|---|---|
| 1-Fe | PS | FS | Inhibition Percent |
| 20 | 0 | 0 | 32 |
| 0 | 5 | 0 | 17 |
| 0 | 0 | 1 | 9 |
| 20 | 5 | 0 | >98 |
| 20 | 0 | 1 | >98 |
| 15 | 0 | 0 | 8 |
| 0 | 5 | 0 | 17 |
| 0 | 0 | 1 | 9 |
| 15 | 5 | 0 | 96 |
| 15 | 0 | 1 | 91 |

1-Fe, PS and FS inhibited the formation of CoA in the HMGCR catalyzed reaction. For analysis of the combined effect of 1-Fe and statins, the statins were used at low concentrations that provide low reaction inhibition, 5 μM of PS and 1 μM of FS that provided 17% and 9% inhibition, respectively. The combinations of 1-Fe with a statin were highly synergistic. For example, 20 μM 1-Fe produced 32% reaction inhibition alone, but in combination with either statin provided more than 98% inhibition. Even when using 1-Fe at a low concentration of 15 μM, that alone provided only 8% reaction inhibition, the combined effect with either statin was still higher than 90%.

This example indicates that statins can be used in combination with corroles such as 1-Fe to provide high levels of HMGCR inhibition, thereby treating CVD and lowering risks of CVD through controlling cholesterol levels. The example further indicates that lower dosages of statins and of 1-Fe may be used in combination to achieve high HMGCR inhibitory effects while limiting risks associated with high concentrations of statin administration.

There is further provided, in accordance with an embodiment of the invention, a method for treatment of a CVD in a subject comprising administering an effective amount of a transition metal complex of a corrole, an optically active isomer thereof or a pharmaceutically acceptable salt thereof in combination with a statin or a pharmaceutically acceptable salt thereof. Optionally, the CVD is selected from the group consisting of: coronary heart disease, primary hyperlipidemia, mixed dyslipidemia, hypertriglyceridemia, dysbetalipoproteinemia, homozygous familial hypercholesterolemia, heterozygous familial hypercholesterolemia, atherosclerosis, congestive heart failure, myocardial infarction, myocardial ischemia and reperfusion. Optionally, the subject suffers from a risk factor associated with CVD selected from the group consisting of: elevated total cholesterol, elevated LDL cholesterol, elevated VLDL cholesterol, elevated apolipoprotein B, elevated triglycerides, decreased HDL cholesterol, elevated oxidized HDL, elevated oxidized LDL, obesity, smoking, type 2 diabetes, type 1 diabetes, history of myocardial infarction, history of revascularization procedures, history of stroke and history of angina. Optionally, the transition metal complex of a corrole has a structure:

wherein $R_1$, $R_2$ and $R_3$ are each independently a carbocyclic aryl ring or a heterocyclic aryl ring, each ring comprising 5 or 6 atoms; M is a transition metal selected from the group consisting of Mn, Fe, Ru, Co, V, Cr, and Cu; $X_1$, $X_2$, $X_3$ and $X_4$ are each independently H or a halogen; $E_2$, $E_3$, $E_{17}$ and $E_{18}$ are each independently H, halogen, $SO_2Cl$, $SO_3H$, $SO_2NR_4R_5$, $CO_2H$, $CO_2R$, $COCl$, $CONR_4R_5$, $CHO$, $CH\!\!=\!\!C(CO_2H)_2$, $CH\!\!=\!\!C(CN)CO_2H)$, or $NO_2$, R is alkyl or aryl and $R_4$ and $R_5$ are each independently H, alkyl, aryl or together with the N atom to which they are attached form a saturated 5-6 membered ring optionally containing an additional heteroatom selected from the group consisting of O, S and N. Optionally, M is Fe or Mn.

Optionally, $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H. Optionally, $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H.

Optionally, the statin is selected from the group consisting of: atorvastatin, cerivastatin, fluvastatin, lovastatin, mevastatin, pitavastatin, pravastatin, rosuvastatin and simvastatin. Optionally the daily corrole dosage is between 0.1 mg and 1500 mg, optionally between 1 mg and 100 mg. Optionally, the transition metal complex of a corrole, an optically active isomer thereof or a pharmaceutically acceptable salt thereof and the statin or a pharmaceutically acceptable salt thereof are administered at the same time. Optionally, the transition metal complex of a corrole, an optically active isomer thereof or a pharmaceutically acceptable salt thereof and the statin or a pharmaceutically acceptable salt thereof are administered in the same dosage form. Optionally, the daily dosage of the statin is a low dose. Optionally, the transition metal complex of a corrole, an optically active isomer thereof or a pharmaceutically acceptable salt thereof the statin or a pharmaceutically acceptable salt thereof are administered through the oral route.

Optionally, the subject suffers from a risk factor after a prolonged treatment regimen of a statin. Optionally, the prolonged treatment is longer than three months, optionally longer than one year. Optionally, the subject was treated with a high dose statin. Optionally, the risk factor is selected from the group consisting of: elevated total cholesterol, elevated LDL cholesterol, elevated VLDL cholesterol, elevated apolipoprotein B, elevated triglycerides, decreased HDL cholesterol, elevated oxidized HDL and elevated oxidized LDL. Optionally, the administration of an effective amount of a transition metal complex of a corrole, an optically active isomer thereof or a pharmaceutically acceptable salt thereof in combination with a statin or a pharmaceutically acceptable salt thereof is effective in lowering at least one risk factor in the subject.

There is further provided in accordance with an embodiment of the invention a method for treatment of a CVD in a subject undergoing treatment using a statin comprising: administering an effective amount of a transition metal complex of a corrole, an optically active isomer thereof or a pharmaceutically acceptable salt thereof; and continuing his statin treatment at a lower dose than the dose administered before corrole administration. Optionally, the statin dose administered after the corrole treatment was initiated is a low dose. Optionally, the subject suffered from an undesirable side effect of statin treatment before initiation of corrole administration. Optionally, the undesirable side effect is selected from the group consisting of: raised liver enzymes, muscle pain, muscle cramps, myalgia, myositis, myopathy, rhabdomyolysis and renal failure.

There is further provided in accordance with an embodiment of the invention a method for lowering cholesterol levels in a subject comprising administering to the subject: an effective amount of a transition metal complex of a corrole, an optically active isomer thereof or a pharmaceutically acceptable salt thereof in combination with a statin or a pharmaceutically acceptable salt thereof. Optionally, the cholesterol level is the total cholesterol level, the LDL level, the oxidized LDL level, the oxidized HDL level, or high triglycerides.

There is further provided in accordance with an embodiment of the invention a pharmaceutical composition comprising: a transition metal complex of a corrole, an optically active isomer thereof or a pharmaceutically acceptable salt thereof; a statin or a pharmaceutically acceptable salt thereof; and a pharmaceutically acceptable carrier. Optionally, the pharmaceutical composition is in the form of a tablet or a capsule. Optionally, transition metal complex of a corrole has a structure:

wherein $R_1$, $R_2$ and $R_3$ are each independently a carbocyclic aryl ring or a heterocyclic aryl ring, each ring comprising 5 or 6 atoms; M is a transition metal selected from the group consisting of Mn, Fe, Ru, Co, V, Cr, and Cu; $X_1$, $X_2$, $X_3$ and $X_4$ are each independently H or a halogen; $E_2$, $E_3$, $E_{17}$ and $E_{18}$ are each independently H, halogen, $SO_2Cl$, $SO_3H$, $SO_2NR_4R_5$, $CO_2H$, $CO_2R$, COCl, $CONR_4R_5$, CHO, CH=C$(CO_2H)_2$, CH=C(CN)$CO_2H$), or $NO_2$, R is alkyl or aryl and $R_4$ and $R_5$ are each independently H, alkyl, aryl or together with the N atom to which they are attached form a saturated 5-6 membered ring optionally containing an additional heteroatom selected from the group consisting of 0, S and N. Optionally, M is Fe or Mn. Optionally, $R_1$, $R_2$ and $R_3$ are each pentafluorophenyl; $E_2$ and $E_{17}$ are $SO_3H$; $X_1$, $X_2$, $X_3$ and $X_4$ are each H; and $E_3$ and $E_{18}$ are H. Optionally, $R_1$, $R_2$ and $R_3$ are each 4-nitrophenyl; $E_2$ and $E_{17}$ are $SO_3H$; $X_1$, $X_2$, $X_3$ and $X_4$ are each H; and $E_3$ and $E_{18}$ are H. Optionally, the statin is selected from the group consisting of: atorvastatin, cerivastatin, fluvastatin, lovastatin, mevastatin, pitavastatin, pravastatin, rosuvastatin and simvastatin. Optionally, the percentage by weight of active ingredients relative to total weight of pharmaceutical composition is between 1% and 70%.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method for treatment of a cardiovascular disease in a subject comprising administering an effective amount of a transition metal complex of a corrole, having the structure:

or a pharmaceutically acceptable salt thereof in combination with a statin or a pharmaceutically acceptable salt thereof, wherein the effect of the statin and the corrole is a synergistic, greater than additive effect.

2. The method according to claim 1 wherein the cardiovascular disease is selected from the group consisting of: coronary heart disease, primary hyperlipidemia, mixed dyslipidemia, hypertriglyceridemia, dysbetalipoproteinemia, homozygous familial hypercholesterolemia, heterozygous familial hypercholesterolemia, atherosclerosis, congestive heart failure, myocardial infarction, myocardial ischemia and reperfusion.

3. The method according to claim 1 wherein the subject suffers from a risk factor associated with cardiovascular disease selected from the group consisting of: elevated total cholesterol, elevated LDL cholesterol, elevated VLDL cholesterol, elevated apolipoprotein B, elevated triglycerides, decreased HDL cholesterol, elevated oxidized HDL, elevated oxidized LDL, obesity, smoking, type 2 diabetes, type 1 diabetes, history of myocardial infarction, history of revascularization procedures, history of stroke and history of angina.

4. The method according to claim 1 wherein the statin is selected from the group consisting of: atorvastatin, cerivastatin, fluva.statin, lovastatin, mevastatin, pitavastatin, pravastatin, rosuvastatin and simvastatin.

5. The method according to claim 1 wherein the daily corrole dosage is between 0.1 mg and 1500 mg.

6. The method according to claim 1 wherein the daily corrole dosage is between 1 mg and 100 mg.

7. The method according to claim 1 wherein the transition metal complex of a corrole, or a pharmaceutically acceptable salt thereof and the statin or a pharmaceutically acceptable salt thereof are administered at the same time.

8. The method according to claim 1 wherein the transition metal complex of a corrole or a pharmaceutically acceptable salt thereof and the statin or a pharmaceutically acceptable salt thereof are administered in the same dosage form.

9. The method according to claim 1 wherein the daily dosage of the statin is a low dose, at a lower dose than the following doses: 10 mg/day wherein the statin is atorvastatin, 0.05 mg/day wherein the statin is cerivastatin, 20 mg/day wherein the statin is fluvastatin, 10 mg/day wherein the statin is lovastatin, 10 mg/day wherein the statin is mevastatin, 1 mg/day wherein the statin is pitavastatin, 10 mg/day wherein the statin is pravastatin, 5 mg/day wherein the statin is rosuvastatin, 10 mg/day wherein the statin is simvastatin.

10. The method according to claim 1 wherein the transition metal complex of a corrole or a pharmaceutically acceptable salt thereof, and the statin or a pharmaceutically acceptable salt thereof, are administered through the oral route.

11. The method according to claim 1 wherein the subject suffers from a risk factor after a prolonged treatment regimen of a statin.

12. The method according to claim 11 wherein the prolonged treatment is longer than three months.

13. The method according to claim 11 wherein the risk factor is selected from the group consisting of: elevated total cholesterol, elevated LDL cholesterol, elevated VLDL cholesterol, elevated apolipoprotein B, elevated triglycerides, decreased HDL cholesterol, elevated oxidized HDL, elevated oxidized LDL.

* * * * *